US00PP37529P2

(12) United States Plant Patent
Horvath

(10) Patent No.: US PP37,529 P2
(45) Date of Patent: Jul. 21, 2026

(54) ***PENSTEMON DIGITALIS* PLANT NAMED 'Pinot Noir'**

(50) Latin Name: *Penstemon digitalis*
Varietal Denomination: Pinot Noir

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 18/831,979

(22) Filed: Dec. 22, 2025

(51) Int. Cl.
*A01H 5/02* (2018.01)
*A01H 6/68* (2018.01)

(52) U.S. Cl.
USPC ..... Plt./465
CPC ..... *A01H 6/68* (2018.05)

(58) Field of Classification Search
USPC ..... Plt./465
CPC ..... A01H 5/02
See application file for complete search history.

*Primary Examiner* — Kent L Bell

(57) ABSTRACT

The new and distinct cultivar of Penstemon plant having dark foliage with purple red coloration in combination with bi-color tubular flowers of purple pink.

1 Drawing Sheet

Figure 1:
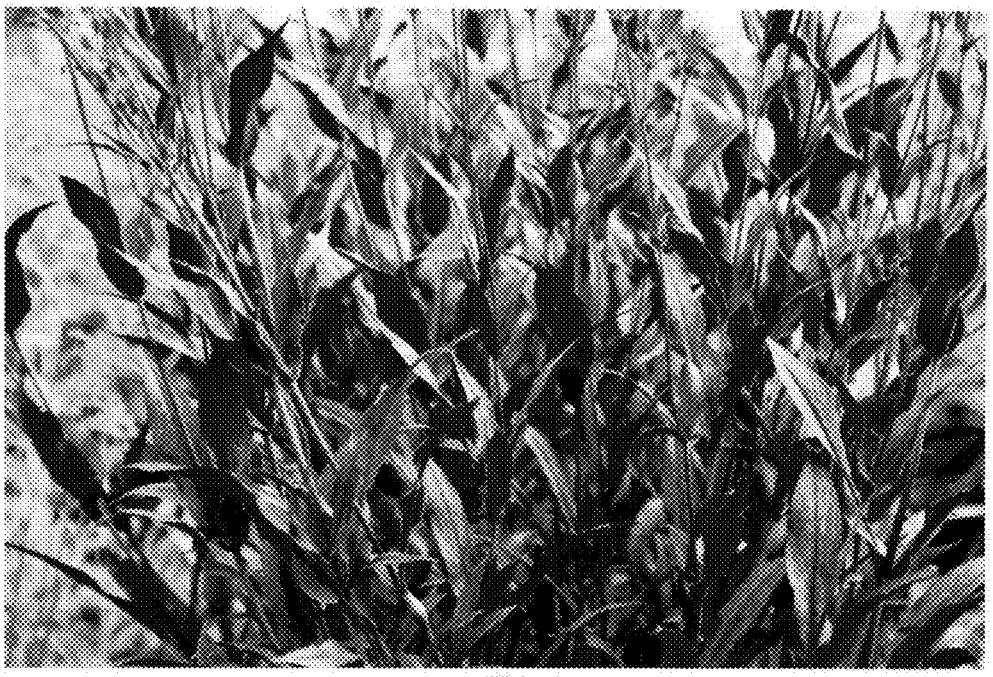

Latin name: *Penstemon digitalis.*
Cultivar name: 'Pinot Noir'.

BACKGROUND OF THE INVENTION

The present invention relates to a new and distinct hybrid of *Penstemon digitalis* plant named 'Pinot Noir' characterized by dark foliage with purple red coloration, in combination with bi-color tubular flowers of purple pink, on substantial plants. The new *Penstemon digitalis* was the result of a breeding program taking place in Hebron, IL U.S. since 2006. The selection of the new plant was due to its' dark foliage with purple red coloration in combination with bi-color tubular flowers of purple pink, on substantial plants. Asexual cutting and division propagation has been the means of reproduction. The intial cutting and division propagation has taken place at a nursery in Hebron, IL since 2020. The new *Penstemon digitalis* has shown to be stable and identical in reproduction to the initially discovered plant after rooting over 2000 plants from 2020 to 2025. No plants of the new *Penstemon digitalis* have been sold in this country, or anywhere in the world, prior to the filing of this application, nor has any disclosure of the new plant been made prior to the filing of this application with the exception of that which was disclosed within one year of filing of this application and was either derived directly or indirectly from the inventor. This includes the inventor's wholesale perennial nursery in Hebron, IL U.S. The first date of sale was made by the inventor's wholesale perennial nursery in 2025. The inventor's wholesale perennial nursery obtained the plant directly from the inventor.

SUMMARY OF THE INVENTION

The new *Penstemon digitalis* plant named 'Pinot Noir' characterized by dark foliage with purple red coloration in combination with tubular flowers of purple pink, on substantial plants, have been observed to be unique and stable. For purpose of the comparison the new plant will be referred to as 'Pinot Noir'.

Plants of 'Pinot Noir' can be compared to the female parent, *Penstemon digitalis* 'Pocahontas', U.S. plant Pat. No. 24,804 patented. 1. The new plant height is typically 85 cm tall while *Penstemon digitalis* 'Pocahontas' is typically 90-100 cm tall. 2. 'Pinot Noir' also has bi-color flowers of 77 B and 76 D while *Penstemon digitalis* 'Pocahontas', has flowers color N82 A.

Plants of 'Pinot Noir' can be compared to the male parent, *Penstemon digitalis* an unnamed white flowered selection, not patented. 1. The new plant height is typically 85 cm tall while *Penstemon digitalis* an unnamed white flowered selection, is typically 60 cm tall. 2. 'Pinot Noir' also has bi-color flowers of 77 B and 76 D while *Penstemon digitalis* an unnamed white flowered selection, has a flower color N155 B.

Plants of 'Pinot Noir' can also be compared to plants of Penstemon hybrid 'Dark Towers', U.S. plant Pat. No. 20,013, patented. 1. 'Pinot Noir' height is typically 85 cm tall while Penstemon hybrid 'Dark Towers' is typically 75 cm tall. 2. 'Pinot Noir' also has two different *Penstemon digitalis* as its parents while Penstemon hybrid 'Dark Towers', has three different species involved in its parentage.

DESCRIPTION OF PHOTOGRAPHS

Figure 2:
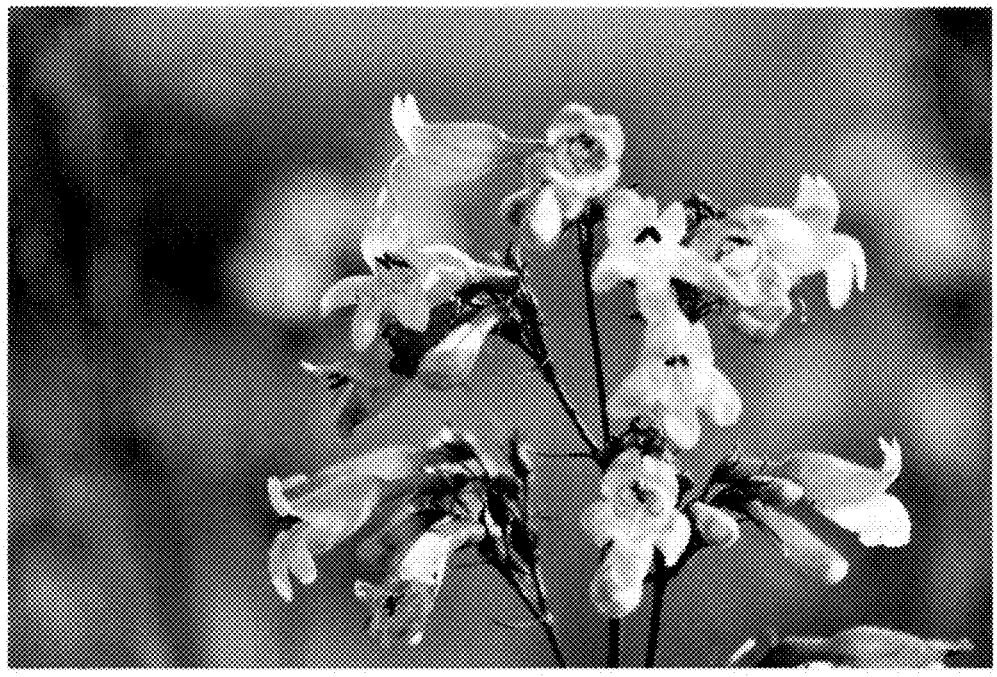

FIG. 1. Foliage in July at a nursery in Hebron, IL U.S.
FIG. 2. Close up of flowers in June at a nursery in Hebron, IL U.S.

DETAILED BOTANICAL DESCRIPTION

In the following description, color references are made to The Royal Horticultural Society Colour Chart copyright 2001. Plants used for the description were grown in the ground for two years at a nursery in Hebron, Illinois. Measurements and numerical values represent averages of typical plants.

Botanical classification: *Penstemon digitalis* cultivar 'Pinot Noir'

Parentage: *Penstemon digitalis* 'Pocahontas' as the female parent and *Penstemon digitalis* an unnamed white flowered selection as the male parent.

Propagation: Vegetative cuttings and division.

Plant Description:

*Type.*—Herbaceous perennial. The overall habit of the new *Penstemon digitalis* is a basal rosette, with thick upright maroon red flower stems topped by bi-color tubular. purple pink flowers on loose clusters in June.

*Hardiness.*—USDA zones 3-8.

*Plant height.*—85 cm.

*Plant width.*—55 cm.

*Stem.*—Diameter — up to 8 mm.

*Stem branches.*—Length: 85 cm.

*Internodes.*—Number: up to 11, length: 9 cm.

*Stem coloration.*—Stem base color varies from purple color N79 B and N79C, to green 146 C, the coloration at the top of the stem is N79 B.

*Stem texture.*—Smooth, glabrous.

*Roots.*—Fibrous, color white close to 155 A.

Foliage description:

*Type.*—Simple, sessile.

*Shape.*—Oblanceolate.

*Arrangement.*—Opposite.

*Leaf Blade size.*—Length: up to 17 cm, Width: 25 mm.

*Margins.*—Serrate.

*Petiole size.*—No petiole observed.

*Leaf apex.*—Acuminate.

*Leaf base.*—Oblique.

*Texture.*—Upper and lower surfaces: smooth, glabrous.

*Adaxial leaf color description.*—N77 A.

*Abaxial leaf color description.*—N79A.

*Venation pattern.*—Pinnate.

*Venation color.*—Upper N77 B, lower N79 B.

*No Lateral leaflets observed.*—

Flower description:

*Inflorescence type.*—Panicle.

*Panicle size.*—Length: 23 cm tall, width: 55 mm.

*Peduncle size.*—Length: 22 mm, diameter: 2 mm.

*Peduncle Texture.*—Smooth, glabrous.

*Peduncle color.*—N79 B.

*Pedicel size.*—Length: 6 mm, diameter: 1 mm.

*Pedicel color.*—N79 B.

*Flower Bud.*—Size: length: 17 mm, diameter: 6 mm.

*Flower Bud surface.*—Slightly pubescent.

*Flower Bud shape.*—Ovoid, tubular, constricted at the base.

*Flower Bud colors.*—Top 77 B, bottom N78 D.

*Corolla description.*—5 petals fused into a tube, constricted at the base.

*Petal apex.*—Entire, obtuse.

*Petal base.*—Fused, constricted.

*Petal margin.*—3 Lower lobes and 2 upper lobes.

*Petal texture.*—Outer surface.—glandular, inside surface: smooth.

*Petal color outer surface.*—Is color 77 B.

*Petal color inside surface.*—Color is 76 D.

*Calyx shape.*—Stellate, campanulate.

*Calyx size.*—Length: 6 mm, Width: 3 mm.

*Calyx color.*—N79 B.

*Sepal arrangement.*—Fused

*Sepal size.*—Length: up to 6 mm, diameter: 1 mm at base coming to a point.

*Sepal quantity.*—5.

*Sepal shape.*—Lanceolate, apex: acute, base: cuneate, margin: entire.

*Sepal texture.*—Upper and lower surfaces: smooth, glabrous.

*Sepal color.*—Adaxial color N79 B, Abaxial color N79 B.

*Flower type.*—Perfect.

*Flower shape.*—Tubular, bilabiate, with 5 petals having 2 upper lobes and three lower lobes, fused into a tube and constricted at the base.

*Flower size.*—Length: 25 mm, width: 14 mm.

*Flower number.*—100 per panicle, 1800 per plant.

*Number of flowering stems.*—15.

*Bloom period and duration.*—Beginning of June in Hebron, IL.

*Flower longevity and duration on the plant.*—Approximately 3 weeks.

*Flower longevity and duration cut.*—not measured.

*Scent.*—None.

Reproductive organs:

*Stamen.*—Quantity: 4, length: 18 mm, diameter: close to 1 mm.

*Anther.*—Quantity: 4, length: 2 mm, diameter: 1 mm.

*Anther shape.*—Oval, color close to 155 B.

*Filament.*—Cream colored at tip near anther, pink at the base.

*Pollen.*—Present, color. white.

*Pistil.*—Number. 1, length: 22 mm, width: 2-3 mm.

*Stigma shape.*—Conical.

*Style.*—Number: 1, length: 17 mm, less than 1 mm wide.

*Ovaries.*—1 with central presentation.

*Fruit.*—Capsule, 12 mm long, 7 mm wide, glabrous, color 166 A.

Disease and Pest Resistance: Resistance to diseases and pests common to Penstemon has not been observed on plants grown under nursery conditions.

Regarding, *Penstemon digitalis* plant named 'Pinot Noir' I claim:

1. A new, distinct *Penstemon digitalis* plant named 'Pinot Noir' substantially as described and illustrated, herein.

* * * * *